United States Patent [19]
Doyle

[11] Patent Number: 4,810,093
[45] Date of Patent: Mar. 7, 1989

[54] VERSATILE AND EFFICIENT RADIATION TRANSMISSION APPARATUS AND METHOD FOR SPECTROMETERS

[75] Inventor: Walter M. Doyle, Laguna Beach, Calif.

[73] Assignee: Laser Precision Corporation, Irvine, Calif.

[21] Appl. No.: 173,562

[22] Filed: Mar. 25, 1988

Related U.S. Application Data

[63] Continuation of Ser. No. 895,211, Aug. 11, 1986, abandoned.

[51] Int. Cl.⁴ ............................................. G01J 3/45
[52] U.S. Cl. .................................................. 356/346
[58] Field of Search ................ 356/346, 244; 350/561, 350/562, 572, 573

[56] References Cited

U.S. PATENT DOCUMENTS

| 3,653,738 | 4/1972 | Gloge. |
| 3,669,522 | 6/1972 | Anderson. |
| 3,748,014 | 7/1973 | Beiser. |
| 3,801,180 | 4/1974 | MaGuire et al. |
| 3,951,526 | 4/1976 | Grossman. |
| 3,977,786 | 8/1976 | Gast ........................ 356/244 X |
| 3,986,767 | 10/1976 | Reter et al. |
| 4,049,945 | 9/1977 | Ehlscheid et al. |
| 4,135,787 | 1/1979 | McLafferty. |
| 4,156,556 | 5/1979 | Klein et al. |
| 4,160,894 | 7/1979 | Stemmler et al. |
| 4,192,573 | 3/1980 | Brown, Jr. |
| 4,215,273 | 7/1980 | Stokes et al. |
| 4,315,130 | 2/1982 | Inagaki et al. |
| 4,367,017 | 1/1983 | Jimbou et al. |
| 4,473,295 | 9/1984 | Doyle ........................ 356/244 |
| 4,475,027 | 10/1984 | Pressley. |
| 4,527,043 | 7/1985 | Hashiura et al. |
| 4,547,068 | 10/1985 | Covey et al. .................. 356/244 |
| 4,657,390 | 4/1987 | Doyle ........................ 356/346 |

Primary Examiner—Davis L. Willis
Assistant Examiner—Matthew W. Koren
Attorney, Agent, or Firm—Thomas J. Plante

[57] ABSTRACT

A spectrometer radiation transmission system is disclosed which permits concurrent availability of numerous alternative accessory devices by conserving radiation throughput. Parabolic reflectors are used to provide alternating collimated and confocal segments of radiation, thereby largely eliminating the problem of vignetting (i.e., loss of radiation throughput due to beam size expansion). Modular enclosure elements are provided, inside which the radiation path travels between the parabolic reflectors.

24 Claims, 3 Drawing Sheets

VERSATILE AND EFFICIENT RADIATION TRANSMISSION APPARATUS AND METHOD FOR SPECTROMETERS

This application is a continuation of application Ser. No. 895,211, filed Aug. 11, 1986 now abandoned.

BACKGROUND OF THE INVENTION

This invention relates to radiation transmission systems which permit radiation, particularly infrared (IR) radiation, to be used in conveying information, such as spectral scanning information obtained by means of Fourier Transform spectroscopy, over relatively long distances and to various alternatively available accessory devices, or sample chambers.

In an earlier application of the same inventor and assignee as this application, U.S. Ser. No. 703,762, filed Feb. 21, 1985, a "Universal Spectrometer System Having Modular Sample Chambers" was disclosed. That application pointed out that traditional interferometer spectrometer systems "for about 40 years" have been "unnecessarily constraining, in terms of the options available to the user of the spectroscopic instrument."

The present application moves even further from the earlier constraints in this field. One of the primary problems heretofore has been the loss of radiation in a non-coherent beam if the distance traveled or the number of optical elements has been extensive. Another problem has been lack of flexibility in making alternative uses of the interferometer spectrometer without complex adjustments and realigning of the optical elements.

A primary purpose of the invention is to provide a family of modular optical devices which allow the beam of an FTIR spectrometer to be routed to and switched between any number of IR sampling peripherals while minimizing signal loss and eliminating the need for optical alignment.

The concepts of the present invention may also be useful outside the field of FTIR spectroscopy.

SUMMARY OF THE INVENTION

The present invention combines confocal and collimated optical segments in an appropriate way to substantially eliminate vignetting (i.e., the loss of energy due to beam growth and the resultant loss of throughput). The use of confocal segments provides pairs of conjugate images, i.e., images in which all of the same rays are present in a matched relationship with respect to angle and location. By the proper arrangement of the optical elements in the system, the limiting aperture of the system can be reimaged at appropriate points in the system. As a result, the inherent spread of the beam is minimized, allowing the maximum possible signal to reach the detector.

The system may include a variety of "position switchable" optical elements, thereby allowing a substantial number of alternative sample compartments, or modules, to be maintained in place for almost instantaneous selection.

In order to conserve radiation, the post-interferometer system is arranged to use reflecting mirrors, e.g., parabolic reflectors, as the focusing optics, rather than lenses, whose refraction and absorption cause throughput reduction.

DETAILED DESCRIPTION OF SPECIFIC EMBODIMENTS

Figure 1:
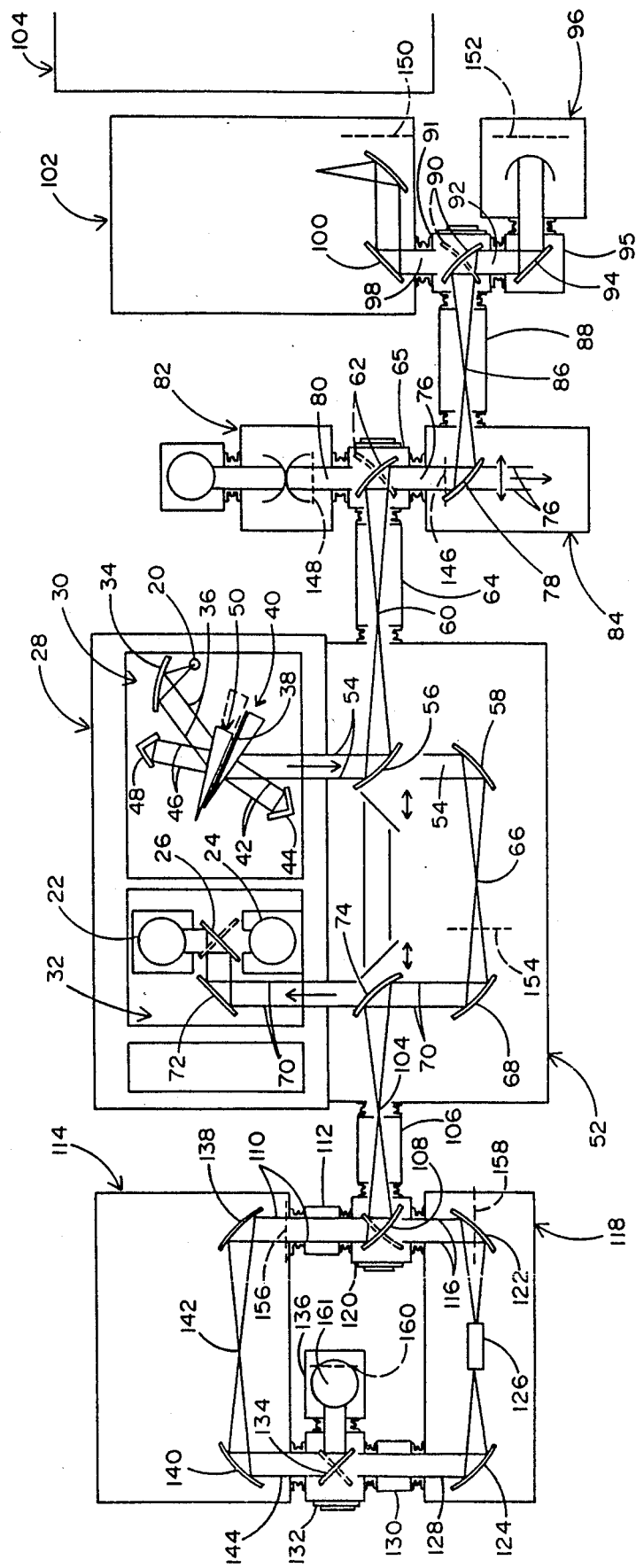
FIG. 1 shows diagrammatically a comprehensive sampling system incorporating the inventive concepts of this application.

In order to provide a rapid understanding of the advantages of the present invention, FIG. 1 shows a reasonably complex example of a multi-option configuration of an interferometer spectrometer system. This is only one of the virtually limitless variety of sampling systems that can be configured for use with a basic spectrometer.

In FIG. 1, the interferometer spectrometer system shown is one marketed by the assignee of this application. The inventive concepts are not, however, limited to that type of system.

The radiation in the system begins with a source 20 and ends with a detector. In the illustrated system, there are two detectors internal to the spectrometer, indicated by numerals 22 and 24. Other detectors are associated with various accessories, or peripherals, in the system. Detectors 22 and 24 have different characteristics, and are selected for separate use by moving a flat mirror 26 between its solid line and dashed line positions.

In FIG. 1, a single structure 28, referred to as the interferometer/detector module, provides an interferometer region 30 and a detector region 32. These regions could be provided as separate modules.

In the illustrated interferometer, which has been shown in several earlier patents and applications, light from source 20 is caused by a reflector 34 to direct a collimated beam 36 toward a beamsplitter coating 38 on one side of a stationary wedge-shaped prism 40. The transmitted portion 42 of the beam is one "arm" of the interferometer, and is reflected back on itself by a stationary retroreflector 44. The reflected portion 46 of the beam is the other "arm" of the interferometer, and is reflected back on itself by a stationary retroreflector 48.

A movable wedge-shaped prism 50 is caused to move between its solid line and dashed line positions, in order to provide the spectral scanning function of the interferometer. This type of scanning, which is referred to as refractive scanning, could be replaced by scanning using a moving mirror (flat mirror or retroreflector) without affecting the relevance of the present invention.

FIG. 1, as an example of the possibilities, combines six different sampling peripherals with the basic modular interferometer/detector unit just described.

A multibeam sample compartment 52 is shown, which is arranged to provide several choices for the operator. A collimated beam 54 enters compartment 52 from the interferometer compartment. A parabolic reflector 56 is mounted on a moving assembly, (not shown). In one position reflector 56 intercepts beam 54; in another position, it does not, thereby permitting collimated beam 54 to reach a stationary parabolic reflector 58.

If beam 54 is reflected from paraboloid 56, it is caused to exit from the right side of compartment 52, focusing at point 60, and then diverging until it reaches a parabolic relfector 62. The paraboloids 56 and 62 are confocal, and the radiation path between them is enclosed in a modular connecting tube, or arm section, 64. The modular tube 64 has a radiation entering port at one end, and a radiation exiting port at the other end. The reflector 62 is itself enclosed in a modular "switching" chamber 65. The modular chamber 65 has a radiation entering port and two alternative radiation exiting ports. The term "confocal" indicates that the two parabolic reflectors have a common focal point; it does not require that they have the same focal lengths.

If paraboloid 56 is in the position in which it does not reflect beam 54, the collimated beam is reflected by paraboloid 58, focusing at point 66, and then diverging until it reaches a stationary confocal parabolic reflector 68, which provides collimated beam 70.

In certain usages, the sample which is illuminated will be at point 66. Then post-illumination beam 70 will return directly to the detector compartment 32, in which it is shown reflected by a flat mirror 72. In such situations, a movable parabolic reflector 74, which is shown in the path of beam 70, will have been moved out of the way of that beam.

With the reflector 56 in the position shown, the scanned interferometer output beam will reach movable paraboloid 62, which, depending on its rotational position, will either direct a collimated beam 76 from the solid line position of reflector 62 toward a parabolic reflector 78, or direct a collimated beam 80 from the dashed line position of reflector 62 toward a diffuse reflectance sampler 82 (which has a detector module 83). The paraboloid 78 is shown as part of the optical system of a microscope 84.

Paraboloid 78 may, as shown, be movable along a translatory path. In one position (not shown), it allows collimated beam 76 to illuminate microscope 84. In the position shown, it causes the radiation to focus at point 86 inside a modular connecting tube, or arm section, 88. After focusing, the beam diverges until it is reflected by a parabolic reflector 90, which is movable inside a modular "switching" chamber 91. Reflector 90 is movable between its solid line and dashed line positions. In the former position it directs a collimated beam 92 toward a flat 45-degree mirror 94, which reflects the beam into a photoacoustic cell 96. In the latter position, it directs a collimated beam 98 toward a flat 45-degree mirror 100, which is integral to a GC/IR (gas chromatograph infrared) interface 102 (having access to a gas chromatograph 104). Flat mirror 94 is mounted inside a modular chamber 95.

If paraboloid 56 is so positioned as to permit collimated beam 54 to reach paraboloid 58, and if paraboloid 74 is in the position shown, collimated beam 70 will be reflected by paraboloid 74 to a focal point 104. The focused beam, which is enclosed by a modular connecting tube, or arm section, 106, then diverges until it is reflected by a parabolic reflector 108. This reflector has two available positions. In its solid line position, it reflects a collimated beam 110, which passes through a modular connecting tube 112 into an automatic sample profiler 114. In its dashed line position, paraboloid 108 reflects a collimated beam 116 into a horizontal access ATR (attenuated total reflectance) sampler 118. The reflector 108 is itself enclosed in a modular "switching" chamber 120.

Inside ATR 118, a pair of confocal parabolic reflectors 122 and 124 cause illumination in a sample container 126. A collimated beam 128 leaving paraboloid 124 passes through a modular connecting tube 130 into a modular "switching" chamber 132, in which a movable flat mirror 134 is mounted. In its dashed line position, mirror 134 directs the radiation from ATR 118 toward a detector module 136.

Inside sample profiler 114, a pair of confocal parabolic reflectors 138 and 140 cause illumination of a sample at 142. A collimated beam 144 leaving paraboloid 140 is reflected by the flat mirror 134, in its solid line position, toward detector module 136.

Each modular unit in the system, including members 52, 64, 65, 82, 84, 88, 91, 95, 96, 102, 106, 112, 114, 118, 120, 130 and 132, has precisely dimensioned flanges at its inlet and outlet openings, each of which flanges engages, and is secured to, a matching flange on the adjacent modular unit. These flanges, when secured together, ensure proper alignment of the optical components in one unit with those in the other units.

It will be apparent, from the foregoing description of an example of a possible combination of modular units, that the operator's experiments can be greatly simplified and accelerated by the ready accessibility of pre-installed sample-analyzing units. While the system can be readily rearranged, if necessary, the possibility of having multiple sample-analyzing units simultaneously in place offers obvious savings in time and effort.

Such a system, however, requires solution of a problem which could eliminate the system's usefulness if unsolved. That problem concerns the need for "conservation of throughput". The natural tendency for such a complex analytical system to lose its radiation intensity between the source and the detector must be overcome.

The primary task of any sampling optical system, such as an FTIR (Fourier Transform infrared) system, is to deliver the maximum possible amount of IR power from the interferometer to the sample and from the sample to an IR detector. The power that can be transmitted by an optical system is proportional to a quantity called its "throughput". This is equal to the area of the system's limiting aperture multiplied by its solid angle field-of-view. In the case of an interferometer, the field-of-view depends on the spectral resolution and on the particular design of the interferometer. For example, the interferometer shown in FIG. 1 is partially field-broadened, yielding a field-of-view of approximately 4 degrees at 2 cm$^{-1}$ resolution.

One of the tenets of optical system design is the "conservation of throughput" principle. This dictates that the throughput of an overall optical system can be no greater than the throughput of its lowest throughput element.

The most straightforward method of interfacing an FTIR spectrometer to a peripheral device is to use the nominally collimated beam obtained directly from the interferometer. This method is usually adequate as long as the peripheral device is within a few inches of the interferometer. But for larger separations, a considerable signal loss will usually occur due to the inherent beam spread corresponding to the field-of-view of the interferometer. For example, with a 4 degree field-of-view, a nominally collimated 1 inch diameter beam will increase in diameter about one inch in a distance of 15 inches. With this amount of beam spread, a significant portion of the beam is likely to fall outside of the usable aperture of a typical sampling system, leading to vignetting of the IR beam and loss of signal.

The present invention eliminates vignetting by taking advantage of the unique properties of confocal optics. Although the system employs reflective optical elements, the principle is equally valid for a design using transmitting lenses. The latter case is used as a simplified illustration (see FIG. 2).

Consider two lenses, L1 and L2, having equal focal lengths f, and separated by a distance equal to 2f. With this lens system, a collimated beam parallel to the system axis (as illustrated by the heavy lines) will be brought to a focus at the common focal point by the first lens, and then recollimated by the second lens. This "confocal" configuration is clearly convenient for use in an optical transfer system, since it provides a standardized collimated output format having the same nominal beam diameter as the input beam.

If an aperture A represents the limiting aperture of the interferometer, imaging theory indicates that this aperture will have an image A' which is conjugate to A, in the sense that all the rays passing through A will also pass through A'. It can be shown that, for the conditions assumed, the separation between A and A' will always be 4f, no matter where A is located relative to the lens system. This simple relationship permits specifying a family of optical systems in which the interferometer aperture is successively reimaged in appropriate planes as the beam passes through the optics, thereby minimizing the effects of vignetting.

Figure 2:
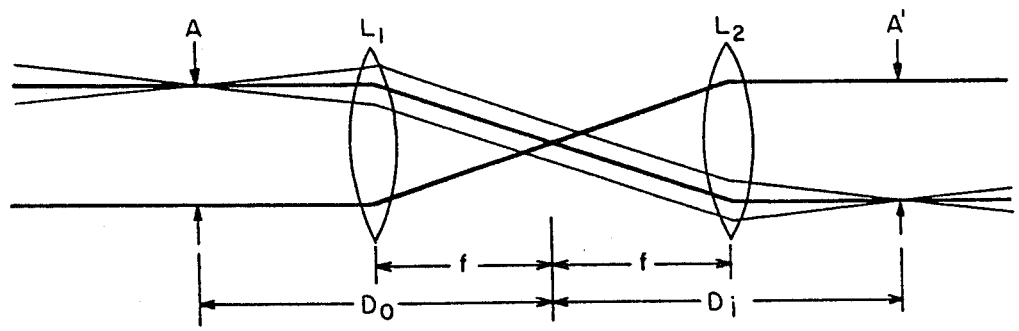
FIGS. 2 and 3 illustrate diagrammatically the optical principles and relationships which guide the present invention.
Figure 3:
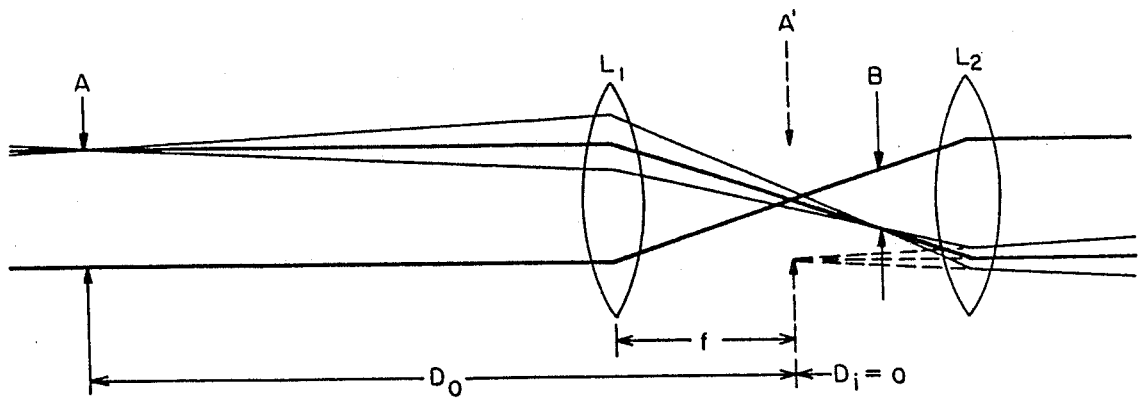

In the example given in FIG. 2, A' is a "real" image of A, in the sense that the optical rays actually pass through the area indicated by A'. In other cases, such as the one illustrated in FIG. 3, A' may correspond to a "virtual" image, because the rays do not actually pass through A' but only appear to a down-stream observer to have come from A'. In this case, B is an intermediate real image formed by the first lens. In either case, the separation between A and A' will be equal to 4f, as noted above.

The same considerations also apply when both the object and the image are downstream from the confocal system. This situation an occur when the "object" of the system is actually an image formed by another imaging system.

The more general case involving confocal optical elements having different focal lengths is somewhat more complicated. If the object distance D(o) and the image distance D(i) are measured from the common focus, it can be shown that:

$$D(i) = (f2/f1)(2f1 + 2f2 - f2D(o)/f1)$$

where f1 and f2 are the focal lengths of the two optical elements, D(o) is taken as positive to the left of the focus, and D(i) is positive to the right of the focus.

In the case of equal focal lengths (f1=f2), this reduces to:

$$D(i) = 4f - D(o), \text{ or } D(i) + D(o) = 4f$$

The focusing elements used in the disclosed system are 90° parabolic reflectors having various focal lengths. A typical confocal section might use a pair of 641 focal length paraboloids, yielding a mirror separation of 12". Minimum beam growth would occur when the interferometer aperture falls 6" in front of the first mirror, yielding a conjugate image 6" beyond the second mirror.

For ideal operation, successive confocal transfer elements should be separated by collimated segments, each providing a total collimated optical path length equal to the mirror separation 2f. In practice, it is not necessary to meet this stringent condition. For example, consider a given nominally collimated region of a system. Assuming a beam diameter d(A) at the position of the conjugate image of the original limiting aperture defined by the rays in this region, an aperture having a diameter d(B) at some point in this region, and a full angle beam spread of α, no vignetting will occur as long as the distance between the plane of the above conjugate image and the plane of the above aperture is equal to or less than $[d(B) - d(A)]/\tan \alpha$. For confocal transfer arms, apertures will occur at or near each of the two parabolic mirrors. It is important that the above condition be met for the collimated regions starting or ending with both of these apertures. For the system manufactured by the assignee of this application, this condition can usually be met by ensuring that an aperture image falls between 0" and 12" between the first mirror of a confocal pair. An analysis of any desired sampling arrangement will suffice to determine the most economical and compact geometry consistent with high optical throughput.

The following is a procedure for designing a high throughput optical system using the principles outlined above. In practice, the process may take considerable trial and error, due to the constraints placed on the system by the physical structures of various major system elements, available space, and conflicting requirements of various sampling systems.

The general procedure outlined below can be followed to minimize the number of required steps in the design process. For illustration, the case of a single interferometer coupled to two or more independent sampling systems will be assumed; also each confocal reflector pair will be assumed to consist of two elements having the same focal length. This will ensure that the throughput of each aperture in a collimated region is proportional to the aperture area, thereby simplifying the analysis.

1: Locate the Limiting Apertures: Examine each of the major elements of the intended system (interferometer, samplers, and detectors); and locate the actual or effective apertures in each that would tend to limit throughput. In most cases, consideration is required only of those apertures which occur in the collimated optical regions, or in the vicinity of a focusing optical element. Location along the optical path, and the approximate diameter, of each aperture must be known. The throughputs of some sampling peripherals, such as ATR accessories, are limited by the angular acceptance in the focused part of the optics. This can be thought of as being equivalent to an effective aperture at the focusing mirror.

2: Select the Critical Path: Determine which of the planned sampling arrangements places the most stringent requirements on optical throughput matching. This will often correspond to the sampling peripheral which has the largest effective optical aperture and hence the greatest throughput. Typical examples of large aperture peripherals are diffuse reflectance and photo-acoustic samplers. Many other types of peripherals—such as GC/IR interfaces, ATR samplers, or FTIR microscopes—have limiting apertures which are considerably smaller than the interferometer or detector apertures. Systems using these peripherals will tolerate a considerable amount of optical mismatch with no noticeable effect.

3: Identify the Smallest Aperture in the Critical Path: The key to an optimized design will be to make sure that all of the radiation which passes through the smallest (i.e.: throughput-limiting) aperture also passes through each of the other apertures. For the steps outlined below, assume that the smallest aperture occurs somewhere in the sampling system.

4: Apply the Following Imaging Rules: Starting from the interferometer aperture, sketch a possible optical layout for the critical path of the sampling system, indicating the positions of each successive image of the interferometer aperture. In doing this, use the $D(i)+D(o)=4f$ rule. Select the focal lengths of the confocal segments and the lengths of the collimated segments so as to accomplish the following objectives:

(a) As far as possible, arrange to have the object for a given confocal segment a distance between 0" and 12" in front of that segment's first mirror.

(b) Establish an image of the interferometer close enough to the sampling system's limiting aperture so that rays which pass through the latter, having the maximum divergence angle allowed by the interferometer, will fall completely within the image of the interferometer aperture.

(c) Continuing past the throughput limiting aperture, establish images of this aperture sufficiently close to any other apertures in the system so that all the rays passing through the throughput-limiting aperture also pass through these other apertures.

5: Add Additional Peripherals, as Needed: Follow the same general procedure as outlined in step 4 for any additional peripherals and/or detectors that need to be simultaneously attached to the FTIR system. To arrive at the optimum compromise between the needs of each sampling system, consistent with the space available, it may be necessary to try several different arrangements for each path of the system.

Using the principles explained above, the system illustrated in FIG. 1 can be analyzed as follows. The effective aperture (e.g., 1" diameter) of the interferometer is at the corner reflectors 44 and 48, a distance of approximately 10" from the interferometer/sample compartment interface, or 13" from the right looking paraboloid reflector 56. Since this reflector and the reflector 62 both have 8" focal lengths, application of the $D(o)+D(i)=2f$ rule enables us to determine that the first image of the interferometer aperture falls 3" beyond the reflecting surface 62, as indicated by the dashed lines 146 and 148. In these planes (146 and 148), all of the radiation from the interferometer—except for that absorbed by the various mirror surfaces—will pass through a 1" diameter effective aperture. Thus no vignetting will occur either at the diffuse reflectance sampler 82 or at the beam switching mirrors in the microscope 84.

Continuing the analysis through the dual 6" confocal arm, it is noted that a second pair of interferometer aperture images 150 and 152 occurs sufficiently close to the focusing optics of the GC/IR interface 102 and the photoacoustic cell 96 to avoid vignetting of the incident beam, and thus allow highly efficient operation of these devices.

Now consider the leftward traveling beam obtained when the beam selection wheel of reflector 56 is switched to an open position and the beam selection wheel of reflector 74 is positioned to provide a converging output beam.

The total distance from the interferometer aperture to the first parabolic mirror 58 is 16". At this distance, the effective diameter of the coherent interferometer beam (at 2 cm$^{-1}$ resolution), which was initially 1 inch, will have spread to about 2.05 inches. Since the parabolic mirror has an effective aperture diameter of 2 inches, vignetting will start to occur. However, at this point, the average power loss due to vignetting for all propagation directions will probably be less than 1%.

For the leftward propagation beam, the first interferometer aperture image will be a virtual image located in the plane indicated by 154. This is reimaged at either 156 or 158, depending on the position of reflector 108, and then reimaged again at 160 slightly behind detector collecting optics 161.

Except for the slight vignetting at the paraboloid 58, noted above, all of the IR beams in this configuration remain well within the acceptance areas of the various optical elements. No other vignetting occurs, except for the inherent vignetting caused by the limited throughputs of the ATR sampler, FTIR microscope, and GC/IR interface.

As indicated in describing FIG. 1, the system preferably consists entirely of modular, interchangeable units. The mechanical construction and interfacing of these units is, in general, the subject of a separate application Ser. No. 900,730 attorney File No. LPC-4. However, a brief summary of the types of modular units will be useful in the present application.

Broadly, the units may be divided into three general categories. The first category includes the modular interferometer/detector unit 28, and the modular sample accessory units 52, 82, 84, 96, 102, 114 and 118. The second category includes the radiation reflecting modules 65, 91, 95, 120 and 132. These radiation reflecting modules may contain parabolic reflectors or planar (flat) reflectors; the positions of their reflectors may be movable or stationary. Also, several of the accessory modules contain movable reflectors. The third category includes the modular connecting tubes 64, 88, 106, 112 and 130.

Figure 4:
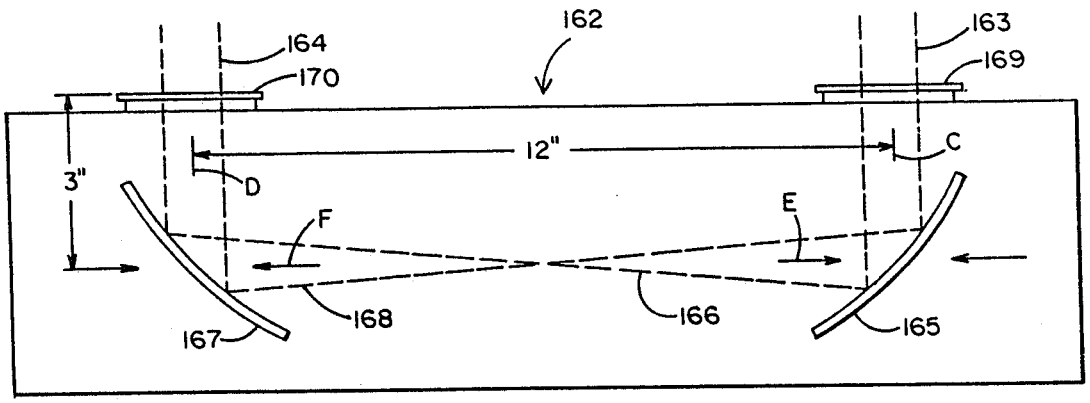
FIG. 4 illustrates diagrammatically the relation of the radiation beam axis to the entering and exiting apertures of each system component.

Since the entire system preferably consists of modular components, it is vital that the collimated and confocal radiation components are correctly oriented, as they enter and exit each modular component. FIG. 4 illustrates this orientation. A modular unit 162 is shown, which has a collimated entering (or exiting) beam 163 and a collimated exiting (or entering) beam 164. It contains a first parabolic mirror 165 between collimated beam 163 and focusing beam 166, and a second parabolic mirror 167 between focusing beam 168 and collimated beam 164.

The axes of both the collimated beams 163 and 164 and the focusing beams 166 and 168 should extend either perpendicular or parallel to the plane of interfacing surfaces 169 and 170, which engage similar interfacing surfaces on the adjacent modular component (or components). Lines C and D lie along the respective axes of collimated beams 163 and 164, and are perpendicular to the plane of interfacing surfaces 169 and 170. Arrows E and F lie along the respective axes of focusing beams 166 and 168, and are parallel to the plane of interfacing surfaces 169 and 170. If the entering and exiting beams were focusing beams, and the beam between reflectors 165 and 167 were collimated, the axes of the focusing beams would be perpendicular to, and the axis of the collimated beam would be parallel to, the plane of interfacing surfaces 169 and 170.

The axis of the beams, both collimated and focusing, is the path traveled by the ray traveling along the center of the collimated beam. In each case, the beam axis may be appropriately referred to as its axis of symmetry. Terms relating to the axes of symmetry of the radiation beams should not be confused with the axes of the parabolic shapes of which the mirrors are segments.

Figure 5:
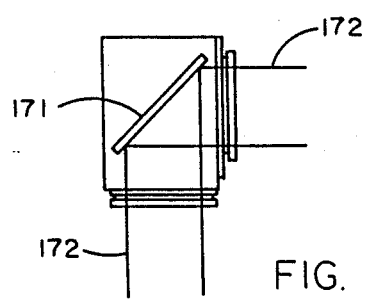
FIGS. 5-11 show schematically seven different modular units containing planar or parabolic mirrors.
Figure 6:
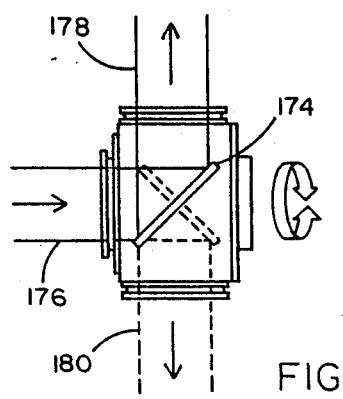

FIGS. 5–11 show schematically seven basic versions of the modular radiation reflecting units. FIG. 5 shows a modular unit having a fixed planar mirror 171, which reflects a collimated beam 172 to change its direction. FIG. 6 shows a modular unit having a planar mirror 174 whose position is rotatable around a vertical axis to direct an incoming collimated beam 176 either in the direction of beam 178 (solid line position) or in the direction of beam 180 (dashed line position).

Figure 7:
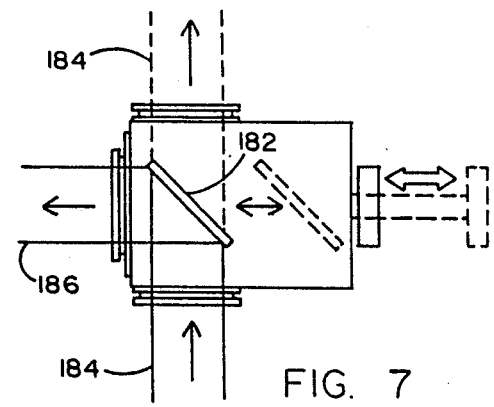

FIG. 7 shows a modular unit having a planar mirror 182 whose position is translational between its solid line position, in which it reflects beam 184 to provide beam 186, and its dashed line position, in which it does not reflect beam 184, permitting the beam to go directly through the modular unit.

Figure 8:
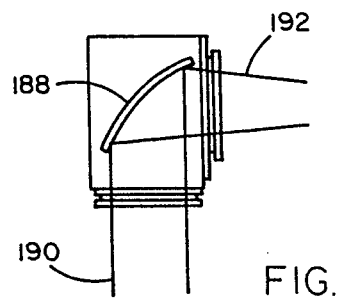

FIGS. 8–11 show different modular units containing parabolic reflectors, which both change the direction of the radiation beam, and change its nature from a collimated beam to a focused beam, and vice versa. In FIG. 8, a fixed parabolic reflector 188 is shown, which can input collimated beam 190 and output (converging) focused beam 192, or input focused (diverging) beam 192 and output collimated beam 190.

Figure 9:
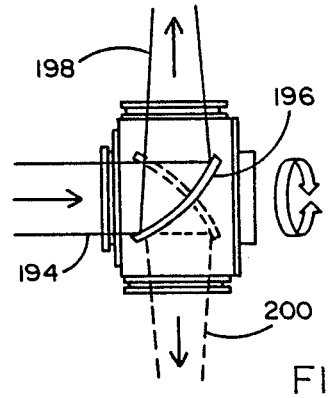
Figure 10:
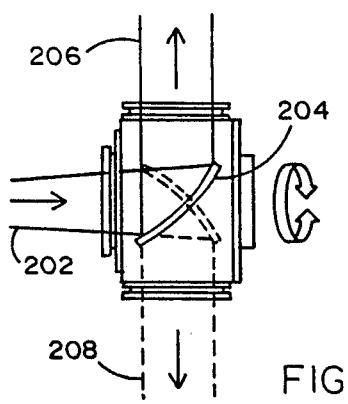

FIGS. 9 and 10 show two modular "switchable" units, each of which has a rotary parabolic reflector, which is capable of directing its output beam in either of two directions. In FIG. 9, the input beam is a collimated beam 194, which is reflected by a parabolic mirror 196. The beam is converted into a converging beam 198 in one direction when mirror 196 is in its solid line position, and is converted into a converging beam 200 in the opposite direction when mirror 196 is in its dashed line position. In FIG. 10, the input beam is a diverging beam 202, which is reflected by a parabolic mirror 204. The beam is converted into a collimated beam 206 in one direction when mirror 204 is in its solid line position, and is converted into a collimated beam 208 in the opposite direction when mirror 204 is in its dashed line position.

Figure 11:
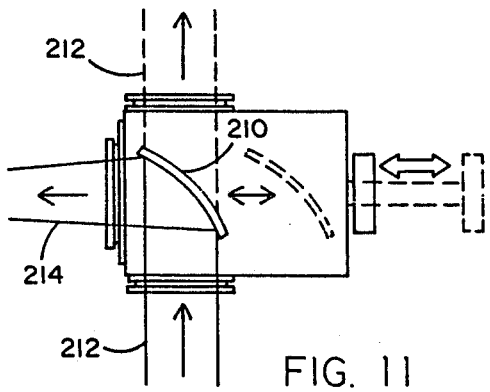

FIG. 11 shows a modular unit having a parabolic mirror 210 whose position is translational between its dashed line position, in which a collimated beam 212 goes directly through the modular unit, and its solid line position, in which collimated beam 212 is reflected by mirror 210 to output a converging beam 214.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. In a spectrometer system which includes a radiation source, an interferometer, a throughput-limiting aperture, and radiation detection means, the effectiveness of which system is dependent on its radiation throughput, a radiation transmission system between the interferometer and the detection means, which comprises:
   at least one collimated segment including optical means for causing the radiation therein to be in collimated form, without substantial diminution of the radiation throughput below that of the throughput-limiting aperture;
   at least one confocal segment including optical means for causing the radiation therein to pass through a focal point between confocal elements, without substantial diminution of the radiation throughput below that of the throughput-limiting aperture; and
   sample-illuminating means which receives the system radiation only after it has passed through both the collimated segment and the confocal segment.

2. The spectrometer radiation transmission system of claim 1 in which the confocal elements of the confocal segment are reflecting mirrors.

3. The spectrometer radiation transmission system of claim 2 in which the confocal elements are parabolic reflecting mirrors.

4. The spectrometer radiation transmission system of claim 3 in which each parabolic reflecting mirror is so positioned and so spaced from other optical elements in the system that all conjugate images of the throughput-limiting aperture are near enough to other apertures in the system to cause substantially all radiation energy which passes through the throughput-limiting aperture to pass through the other apertures.

5. The spectrometer radiation transmission system of claim 3 in which one of the confocal parabolic mirrors receives a collimated incoming beam and reflects it as a focusing beam directly to the confocal point, and the other of the confocal parabolic mirrors receives a diverging beam directly from the confocal point and reflects it as an outgoing collimated beam.

6. The spectrometer radiation transmission system of claim 5 in which each of the confocal parabolic mirrors directs the axis of symmetry of its outgoing beam along a path perpendicular to the axis of symmetry of its incoming beam.

7. The spectrometer radiation transmission system of claim 3 in which the confocal segment includes:
   a tube-like elongated element which provides an enclosure for only one confocal radiation beam.

8. The spectrometer radiation transmission system of claim 7 in which the confocal segment also includes:
   a chamber element which provides an enclosure for only a single parabolic mirror which receives an incoming confocal radiation beam and reflects it as an outgoing collimated beam traveling in a different direction.

9. The spectrometer radiation transmission system of claim 8 in which the axis of symmetry of the outgoing collimated beam is perpendicular to the axis of symmetry of the incoming confocal beam.

10. The spectrometer radiation transmission system of claim 3 in which the confocal segment includes:
    a chamber element which provides an enclosure for only a single parabolic mirror which receives an incoming confocal radiation beam and reflects it as an outgoing collimated beam traveling in a different direction.

11. The spectrometer radiation transmission system of claim 10 in which the axis of symmetry of the outgoing collimated beam is perpendicular to the axis of symmetry of the incoming confocal beam.

12. The spectrometer radiation transmission system of claim 1 in which each confocal element is large enough to receive substantially all incoming radiation.

13. The spectrometer radiation transmission system of claim 1 in which:
the throughput-limiting aperture of the system is in a collimated segment of the radiation system;
a conjugate image of the throughput-limiting aperture is defined by rays in another collimated segment of the radiation system;
the radiation in the latter collimated segment passes through a different aperture; and
the distance between said different aperture and the conjugate image is such that substantially no radiation energy is rejected by said different aperture.

14. The spectrometer radiation transmission system of claim 13 in which the distance between the conjugate image and said different aperture is no greater than $d(B)-d(A)/\tan \alpha$, where $d(A)$ represents the beam diameter at the position of the conjugate image, $d(B)$ represents the diameter at said different aperture, and $\alpha$ represents the full angle beam spread of the collimated beam in this region.

15. The spectrometer radiation transmission system of claim 13 in which the location of the conjugate image is determined by the locations and focal lengths of two confocal elements.

16. The spectrometer radiation transmission system of claim 1 which comprises:
a plurality of collimated segments; and
a plurality of confocal segments which alternate with the collimated segments, so that a collimated beam portion enters or exits each of the confocal elements.

17. The spectrometer radiation transmission system of claim 16 in which:
the throughput-limiting aperture has a collimated beam passing therethrough; and
the positions of the apertures and optical elements in the system are such as to position any image of the throughput-limiting aperture near enough to other apertures and reflectors in the system so that substantially all energy which passes through the throughput-limiting aperture also passes through the rest of the system.

18. A spectrometer system comprising:
an interferometer which outputs a collimated beam;
a first radiation transmission segment comprising first and second confocal elements;
the first confocal element reflecting the collimated beam from the interferometer toward an unobstructed first focal point;
the second confocal element collecting and reflecting the beam diverging from the unobstructed first focal point to provide a collimated beam; and
a second radiation transmission segment comprising third and fourth confocal elements;
the third confocal element reflecting toward a second focal point the collimated beam from the second confocal element; and
the fourth confocal element collected and reflecting the beam diverging from the second focal point.

19. A spectrometer radiation transmission system comprising:
means for providing an analytical radiation beam;
a first collimated radiation segment emanating from said means;
a confocal radiation segment receiving the radiation from the collimated radiation segment, and transmitting such radiation substantially unchanged;
a second collimated radiation segment receiving the radiation from the confocal radiation segment; and
a sample-analyzing means receiving the radiation subsequent to its travel through the foregoing radiation segments.

20. The spectrometer radiation transmission system of claim 19 wherein the confocal segment is provided by two parabolic reflecting mirrors having a common focal point.

21. In a spectrometer system which is adopted to illuminate a sample, and which includes a source of spectral scanning radiation and radiation detection means, a multiple unit modular pre-sample radiation transmission system comprising:
one or more first modular elements in the form of connecting tubes each adapted to enclose a single radiation beam traveling through the element in a linear directions;
one or more second modular elements in the form of chambers each adapted to enclose a single radiation beam entering and exiting the element in different directions;
means for securing together a plurality of the first and second modular elements; and
a series of parabolic mirrors which cause reflected radiation to travel inside the first and second modular elements in such a way that collimated beam segments alternate with confocal beam segments;
each parabolic mirror having as its incident and reflected beams unobstructed collimated or confocal beams traveling from or toward the next parabolic mirror in the series.

22. The pre-sample radiation transmission system of claim 21 in which the incident and reflected beams at each parabolic mirror are at right angles to one another.

23. The pre-sample radiation transmission system of claim 22 in which each modular element has a beam-entering port and a beam-exiting port, each of which is surrounded by a flat interfacing surface lying in a plane perpendicular to the axis of symmetry of the beam which passes through such port.

24. The pre-sample radiation transmission system of claim 23 which also comprises:
means for coupling adjacent modular elements in such a way as to allow relative position adjustment of the coupled modular elements around the axis of symmetry of the enclosed radiation beam.

* * * * *